Figure 2B:
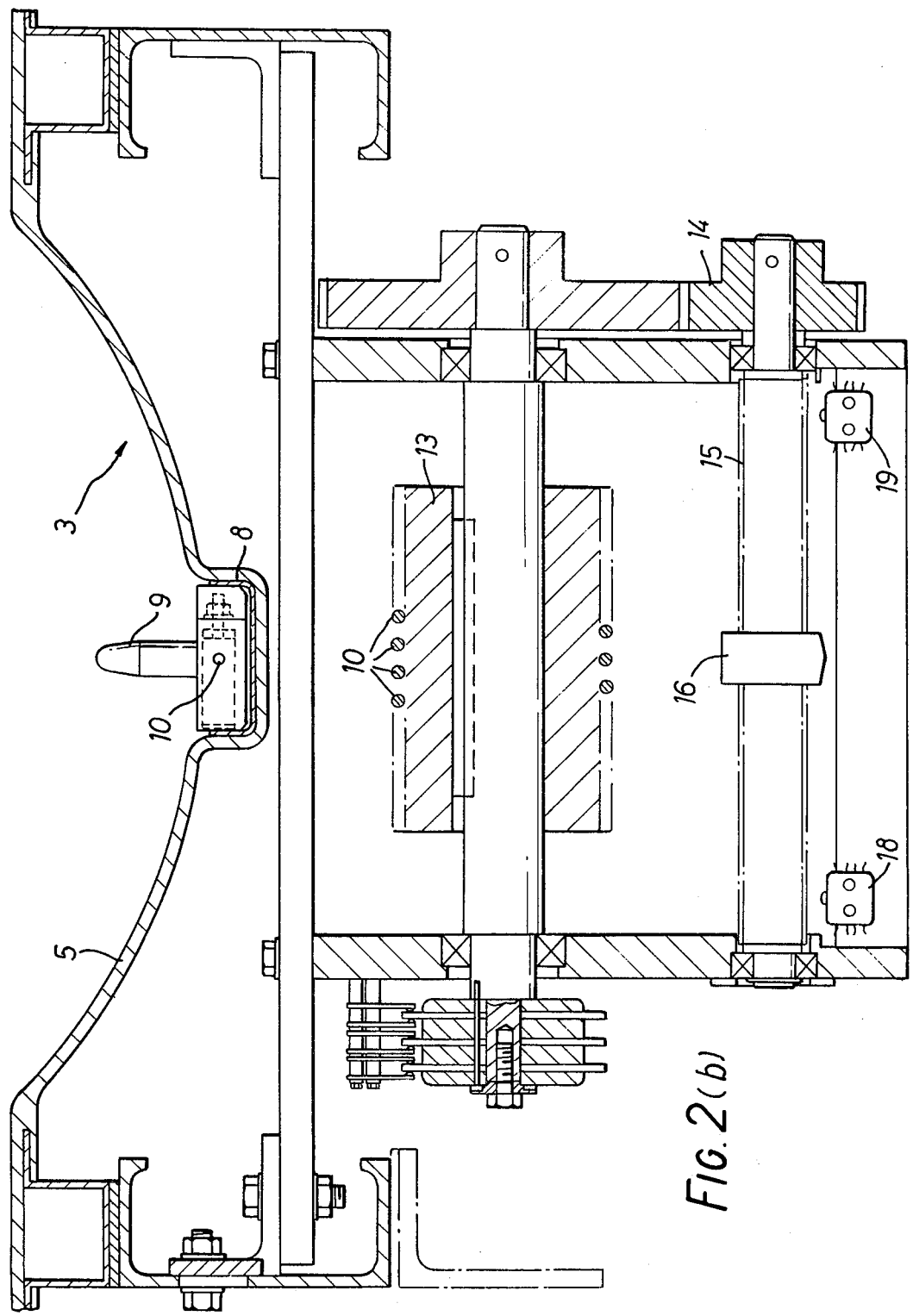

United States Patent [19]

Heavens et al.

[11] 4,034,224
[45] July 5, 1977

[54] PATIENT POSITIONING AND SUPPORTING ARRANGEMENT

[75] Inventors: Michael Heavens, Hillingdon; Richard Charles James, Uxbridge; Dennis Stanley Slinn, West Drayton, all of England

[73] Assignee: EMI Limited, Hayes, England

[22] Filed: Apr. 12, 1976

[21] Appl. No.: 676,056

[30] Foreign Application Priority Data

Mar. 25, 1976 United Kingdom ............ 11959/76

[52] U.S. Cl. .................. 250/439 P; 250/445 T; 250/456; 269/323
[51] Int. Cl.² ............................... H01J 37/20
[58] Field of Search ...... 250/439, 442, 444, 445 R, 250/445 T, 446, 449, 451, 456, 491; 269/323

[56] References Cited
UNITED STATES PATENTS

| | | | |
|---|---|---|---|
| 1,374,235 | 4/1921 | Richards | 250/444 |
| 3,449,570 | 6/1969 | Kok | 250/456 |
| 3,501,634 | 3/1970 | Roesch | 250/444 |
| 3,576,997 | 5/1971 | Slavin | 250/439 |
| 3,588,500 | 6/1971 | Koerner | 250/439 |
| 3,947,686 | 3/1976 | Cooper et al. | 250/451 |
| 3,974,388 | 8/1976 | Distler et al. | 250/456 |

*Primary Examiner*—Alfred E. Smith
*Assistant Examiner*—B. C. Anderson
*Attorney, Agent, or Firm*—Cooper, Dunham, Clark, Griffin & Moran

[57] ABSTRACT

A positioning and supporting arrangement for a patient to be irradiated with penetrating radiation is disclosed. The patient is supported on a curved platter, the curvature of which conforms to the curvature of an arcuate groove formed longitudinally in a table or couch. In order that the platter may be slidably moved along the groove, a suitable drive means therefor is described. Preferably a shroud covers the underside of the platter, the shroud being formed of, or including, material which provides a well defined, consistent coefficient of friction between the platter and the table or couch.

9 Claims, 4 Drawing Figures

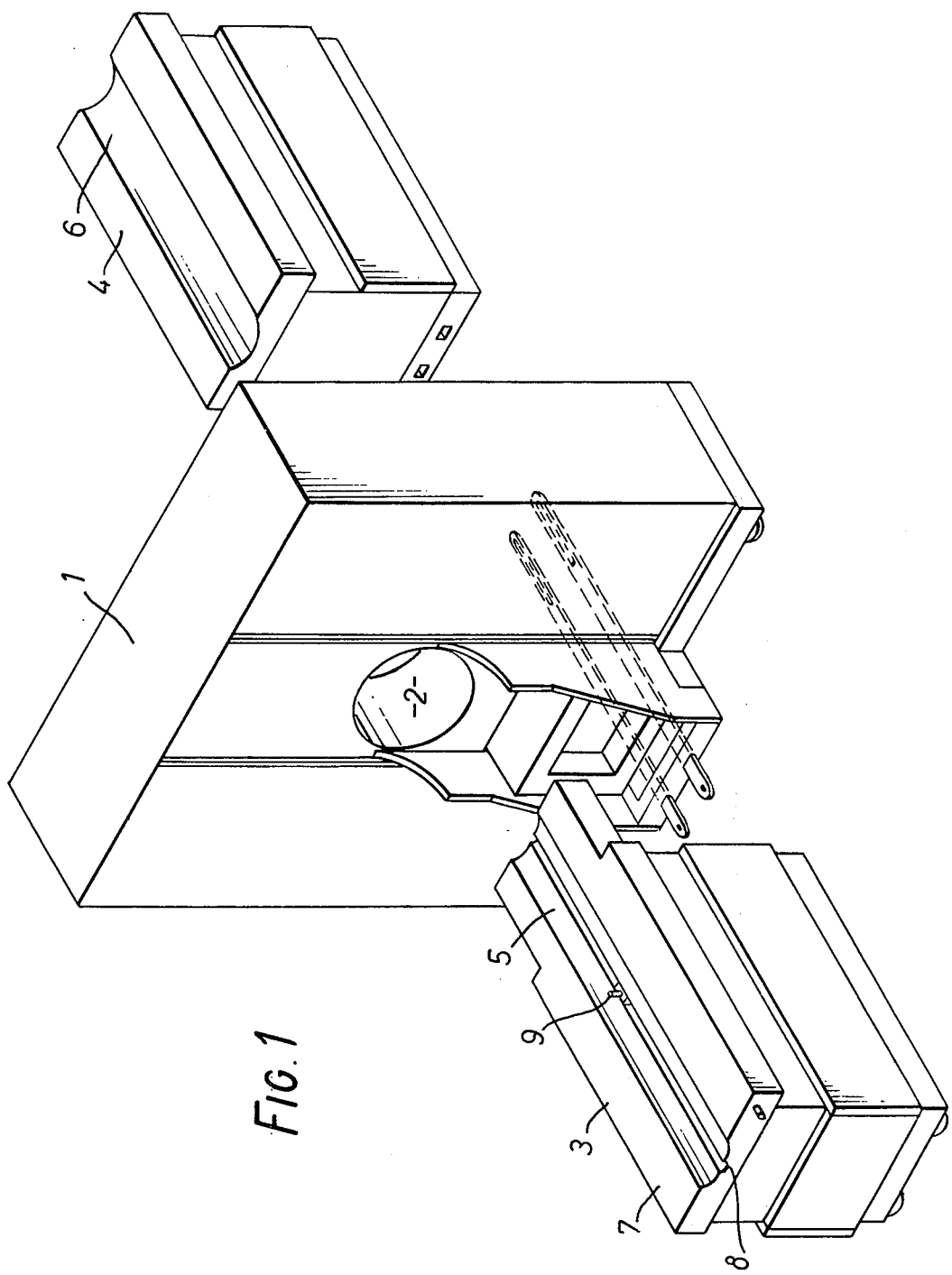

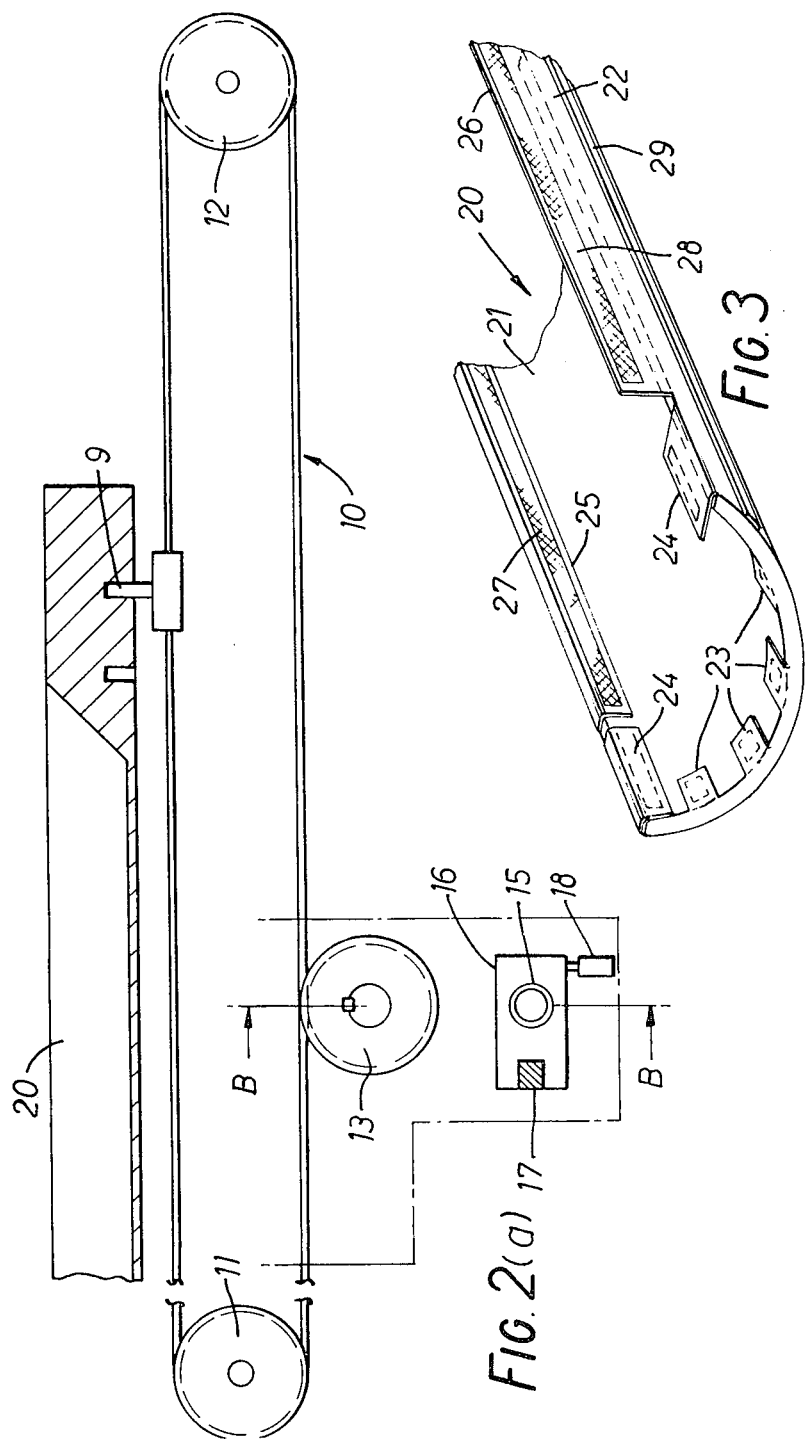

PATIENT POSITIONING AND SUPPORTING ARRANGEMENT

The present invention relates to a patient positioning and supporting arrangement which is especially, though not exclusively, suitable for use with an apparatus which is capable of being used to examine a part of the patient's body by a radiographic technique known as computerized axial tomography. Apparatus for performing computerized axial tomography is described and claimed in U.S. Pat. No. 3,778,614.

In essence, computerized axial tomography is performed by measuring the absorption suffered by X-radiation on traversing each of many substantially co-planar, pencil-like beam paths through a body and processing signals indicative of the various absorption values to evaluate the absorption coefficient, with respect to the radiation used, at each of a number of locations distributed over the substantially planar region of the body traversed by the beam paths. The processing is preferably effected without transforming the absorption values out of the spatial domain, and suitable processing techniques are described in the aforemention U.S. Patent and in U.S. Pat. No. 3,924,129. A visual representation of the evaluated coefficients is provided in any convenient manner.

The patient's body must be positioned properly and supported in a suitable manner while the examination is carried out, and it is an object of this invention to provide a patient positioning and supporting arrangement for this purpose.

According to the invention there is provided an arrangement for positioning and locating the body of a patient in relation to an apparatus for irradiating the body with penetrating radiation, the arrangement comprising a curved platter upon which the patient can be disposed, a table having a curved groove to accommodate the platter, and means for driving the platter slidably along the groove; the platter comprising a substantially rigid platform shaped to conform to said curve. Preferably, a shroud is secured to the platter and disposed, in operation, between the platter and the surface of said groove, so as to permit the platter to slide smoothly in said groove.

In order that the invention may be clearly understood and readily carried into effect, one embodiment thereof will now be described, by way of example only, with reference to the accompanying drawings of which:

FIG. 1 shows, in perspective view, apparatus incorporating the invention, but does not show the platter, FIG. 2 comprises FIG. 2(a) which shows, in side elevation a suitable arrangement for driving the platter, and FIG. 2(b) which shows a detailed cross-section on lines B—B of FIG. 2(a), and FIG. 3 shows, in perspective view, a platter suitable for use, in accordance with the invention, with the apparatus shown in FIG. 1.

Referring now to the drawing, the apparatus shown in FIG. 1 comprises a central housing 1, which is formed with an aperture 2, in which a body to be examined can be located, and front and rear couches 3 and 4 respectively which usually remain fixed relative to the housing 1 but are removable therefrom should the need arise.

The housing 1 contains, among other things, the active elements of a computerized axial tomographic apparatus, i.e. a source of X-radiation and a bank of radiation sensitive detectors mounted on a scanning gantry which is capable of executing both translational and rotational scanning movements about the aperture 2. A suitable arrangement of source, detectors and scanning gantry and appropriate operating procedures therefor is described in detail in U.S. Pat. No. 3,946,234 and thus will not be further described herein.

It is stressed, however, that the arrangement disclosed in the aforementioned U.S. Pat. No. 3,946,234, while having been proved in practice to operate well, is not the only arrangement which could be used. For example it may be preferred to utilise a source of a spread of X-radiation which substantially irradiates the entire profile of the body in the plane to be examined, together with a correspondingly enlarged bank of detectors, to enable the translational scanning movement to be dispensed with altogether, as described in U.S. Pat. No 3,937,963, or to be effected, on a reduced scale, by means of an X-ray tube having facilities whereby the electron beam thereof can be deflected over an elongated target/anode as described in U.S. patent application Ser. No. 630,779. In either event, the only mechanical scanning movement required is a rotational one.

Whichever technique is employed, and in this example it is the one involving both translational and rotational mechanical-scanning movements as described in U.S. Pat. No. 3,946,234, radiation projected through the body along many co-planar, pencil-like beam paths is detected by the detectors. The absorption suffered by the radiation in traversing each beam path is determined, and the absorption values so determined are processed, for example in accordance with the technique disclosed in U.S. Pat. No. 3,778,614 or in accordance with the technique disclosed in U.S. Pat. No. 3,924,129 to evaluate the absorption coefficient at each of a plurality of locations distributed over the irradiated plane of the body.

The patient's body, as previously mentioned, has to be properly supported whilst the examination is carried out so that a plane of interest in the body coincides with the plane irradiated by the source of X-radiation. To this end, the front and rear couches 3 and 4 are formed with longitudinally extending arcuate grooves 5 and 6 respectively. The flat horizontal surfaces (e.g. that shown at 7) of the couches 3 and 4 are covered with Formica having a smooth finish so that they can be easily wiped clean should they be soiled, whereas the faces of the grooves 5 and 6 are covered with Formica having a matt finish to provide a well defined coefficient of friction which is substantially constant throughout the length of the grooves.

In the base of the groove 5 in the front couch 3 there is formed a channel 8 in which is disposed a drive wire (not shown in FIG. 1) to which a drive spigot 9 is secured. The drive wire, as will be more fully explained with reference to FIG. 2, passes over a pulley at either end of the front couch 3 and back underneath itself to be wrapped around a drum which is driven by an electric motor.

The platter, which will be more fully described with reference to FIG. 3, is in the form of a rigid stretcher which is curved to fit the grooves 5, 6. The base of the stretcher is formed, adjacent one end thereof, with a hole into which the drive spigot 9 slots. The platter can then be driven into and through the aperture 2 by means of the drive arrangement just described.

Referring now to FIGS. 2(a) and 2(b) which show respectively a schematic side elevational view and a detailed cross-sectional view taken on the lines B—B in FIG. 2(a), it can be seen that the drive spigot 9 is secured to a cable 10 which constitutes the aforementioned drive wire. The cable is a plastic-covered braided wire cable and is effectively endless; the two ends being joined at the spigot 9. As previously mentioned, the cable 10 runs along the channel 8 in the front couch 3 and passes over a pair of idler pulleys 11 and 12 disposed at respective ends of the couch 3. The cable 10 then passes back beneath the channel 8 and is wound in three turns around a drive drum 13. The drum 13 is driven by an electric motor (not shown) by way of a gearing arrangement. As the drum 13 rotates it drives a wheel 14 (FIG. 2(b)) which, in turn, drives a lead screw 15. Mounted on the lead screw, so as to traverse therealong when the lead screw 15 rotates, is an actuator 16. The actuator 16 also runs on a guide 17 (FIG. 2(a)) to prevent it rotating with the lead screw. The pitch of the lead screw 15 is arranged so that, when the spigot 9 is at its closest permissible approach to the idler pulley 11, the actuator 16 contacts the operating member of a micro-switch 18 which disconnects the electrical power to the motor which drives the drum 13, thus preventing further movement of the spigot 9 towards the idler wheel 11. Similarly, when the spigot is driven in the opposite direction, towards idler wheel 12, the actuator 16 approaches a second micro switch 19 (FIG. 2(b)); the arrangement being such that, when the spigot has travelled as far as necessary in that direction, the actuator 16 operates the micro-switch 19 so as to disconnect the electrical power to the motor which drives the drum 13.

The platter, which is shown generally at 20 in FIG. 2(a), is shown in more detail in FIG. 3 and consists of an elongated, rigid stretcher 21 formed of either laminated formica or wood and shaped to fit the curvature of the grooves 5 and 6. Stretched over the base of the stretcher is a nylon shroud 22 which is secured to the stretcher by means of strips of the material known as "Velcro" co-operating with other Velcro strips formed on material attached to the stretcher 21 at its ends as shown at 23 and at the sides thereof adjacent the ends as shown at 24. Along most of the length of the stretcher the nylon shroud is formed with flaps 25 and 26 formed with respective Velcro strips 27 and 28 to which a suitable belt can be secured; the belt being used to hold the patient firmly in the platter, and having Velcro strips secured to its ends.

The nylon shroud 22 is similar in appearance to cheese-cloth and has been found to exhibit suitable sliding characteristics on the matt Formica finish in the grooves 5, 6. In addition, four strips such as 29 of P.T.F.E. (polytetrafluoroethylene) are secured to the underside of the shroud, running longitudinally thereof and extending the full length of the platter. These strips are provided to reduce fraying of the nylon material forming the shroud because of its tendency to ruck and pucker, especially at the commencement of movement of the platter relative to the couches. The P.T.F.E. strips also improve the coefficient of friction between the platter and the couches.

In some circumstances, it may be desired to move the platter 20 incrementally relative to the couches 3 and 4. This can be effected automatically under the influence of one or more graticule discs and suitable photo-cell/detector arrangements. It is preferred, however, to provide a manually operable incrementing arrangement by means of which the platter is moved incrementally through a predetermined distance in response to the manual operation of a push button. The predetermined distance can be selected from three alternatives, e.g. 5cm, 10cm and 15cm. If several incremental movements are required, the push button has to be operated a corresponding number of times. If neither of the three push buttons is actuated, the platter is automatically moved through a distance of 13mm between scans.

It is preferable for the motor which drives the cable drum 13 to be a two speed motor. This enables a patient originally supported by the front couch 3 to be transported rapidly through the aperture 2 until he is in approximately the desired position for examination, at which time the motor is switched to its lower operating speed to enable the operator to position the body accurately in the aperture 2.

Although they are not shown in the drawings, it is preferable for a number of touch-sensitive switches to be provided in the aperture 2. These switches can be linked to the controls of the apparatus in known manner so as to inhibit the scanning operation and/or certain movements of the platter should a part of the patient's body contact the housing 1.

Instead of the nylon shroud 22 with its P.T.F.E. strips, it is possible, and sometimes preferable, to use a shroud formed of a material known as "TYGAFLOR 128A/10T" which is a P.T.F.E. coated glass fabric. This material has a more suitable coefficient of friction with respect to the couches, and has increased resistance to fraying as compared with the nylon shroud referred to previously.

What we claim is:

1. An arrangement for positioning and locating the body of a patient in relation to an apparatus for irradiating the body with penetrating radiation, the arrangement comprising a curved platter upon which the patient can be disposed, a table having a curved groove to accommodate the platter, and means for driving the platter slidably along the groove; the platter comprising a substantially rigid platform shaped to conform to said curved groove.

2. An arrangement according to claim 1 including a shroud of selected friction characteristics secured to said platter and disposed, in operation, between the platter and the surface of said groove so as to permit the platter to slide smoothly in the groove.

3. An arrangement according to claim 2 wherein the material of which said shroud is formed in nylon.

4. An arrangement according to claim 3 wherein strips of P.T.F.E. are formed on the underside of the shroud, the strips being disposed lengthwise of said platter.

5. An arrangement according to claim 2 wherein the material of which said shroud is formed in a glass fabric coated with P.T.F.E.

6. An arrangement according to claim 1 wherein the table includes means defining a channel extending along the base of said groove and the means for driving said platter along the groove includes a drive wire set in said channel, a drum, beneath the table, around which said drive wire is wrapped, a motor for rotating said drum and a spigot secured to said drive wire and located in said channel; the platter being formed with an aperture in its base to accommodate said spigot.

7. An arrangement according to claim 6 including means operated in response to rotation of said drum to inhibit motion of said drive wire when said spigot approaches either end of said channel.

8. An arrangement according to claim 1 including an apertured housing, the dimensions of the aperture thereof being sufficient to permit traversal therethrough of the platter and a patient borne thereon; and a second table formed with a similar arcuate groove and disposed at the side of the housing opposite that of the table provided with a drive means for driving said platter, the two tables being aligned with each other to allow the platter to move from one to the other.

9. An arrangement according to claim 8 wherein said housing contains the active elements of a computerised axial tomographic apparatus.

* * * * *